United States Patent
Bonfiglioli

(10) Patent No.: US 9,074,960 B2
(45) Date of Patent: Jul. 7, 2015

(54) METHOD AND APPARATUS FOR CHECKING SYRINGE BODIES

(71) Applicant: BONFIGLIOLI ENGINEERING S.r.l., Vigarano Mainarda (Ferrara) (IT)

(72) Inventor: Giuseppe Bonfiglioli, Sant'Agostino (IT)

(73) Assignee: BONFIGLIOLI ENGINGEERING S.R.L. (IT)

( * ) Notice: Subject to any disclaimer, the term of this patent is extended or adjusted under 35 U.S.C. 154(b) by 0 days.

(21) Appl. No.: 14/202,680

(22) Filed: Mar. 10, 2014

(65) Prior Publication Data
US 2014/0290344 A1    Oct. 2, 2014

(30) Foreign Application Priority Data

Mar. 26, 2013   (IT) ............................... BO2013A0128

(51) Int. Cl.
| G01M 3/34 | (2006.01) |
|---|---|
| G01M 3/02 | (2006.01) |
| G01M 3/32 | (2006.01) |
| A61M 5/31 | (2006.01) |

(52) U.S. Cl.
CPC .............. *G01M 3/02* (2013.01); *G01M 3/3209* (2013.01); *G01M 3/3281* (2013.01); *G01M 3/34* (2013.01); *A61M 2209/02* (2013.01); *A61M 2005/3121* (2013.01); *A61M 2205/15* (2013.01)

(58) Field of Classification Search
CPC ... G01M 3/02; G01M 3/3209; G01M 3/3281; G01M 3/34; A61M 2005/3121; A61M 2205/15; A61M 2209/02

USPC ......................... 73/40.7, 49.3; 604/19; 29/777
See application file for complete search history.

(56) References Cited

U.S. PATENT DOCUMENTS

| 3,762,212 | A | * | 10/1973 | Morley et al. .................. 73/40.7 |
|---|---|---|---|---|
| 3,824,840 | A | * | 7/1974 | Amberg ......................... 73/45.3 |
| 4,934,180 | A | * | 6/1990 | Hulsman ........................ 73/49.3 |
| 5,042,291 | A | * | 8/1991 | Lehmann ....................... 73/49.3 |
| 5,111,684 | A | * | 5/1992 | Stauffer et al. ................ 73/49.3 |
| 5,226,316 | A | * | 7/1993 | Mally et al. ................... 73/49.3 |
| 5,513,516 | A | * | 5/1996 | Stauffer ........................ 73/49.2 |
| 5,939,619 | A | * | 8/1999 | Achter et al. .................. 73/40.7 |
| 6,082,184 | A | * | 7/2000 | Lehmann ....................... 73/49.3 |
| 6,305,215 | B2 | * | 10/2001 | Lehmann ....................... 73/49.3 |

(Continued)

FOREIGN PATENT DOCUMENTS

WO    2008/012611    1/2008

OTHER PUBLICATIONS

Italian Search Report dated Jan. 22, 2014 from counterpart App No. BO20130128.

*Primary Examiner* — Laura Martin
*Assistant Examiner* — Samir M Shah
(74) *Attorney, Agent, or Firm* — Timothy J. Klima; Shuttleworth & Ingersoll, PLC

(57) ABSTRACT

Described is a method for checking syringe bodies of the type comprising a hollow body, a seal for closing the hollow body and a dose of a liquid product enclosed by the hollow body and by the seal, the method comprising the steps of applying a pneumatic negative pressure to the syringe body and moving a stop body towards the syringe body in such a way that, during at least a part of the step of applying the pneumatic negative pressure, the stop body obstructs withdrawal of the seal towards a rear end of the syringe body opposite the liquid.

15 Claims, 6 Drawing Sheets

(56) References Cited

U.S. PATENT DOCUMENTS

| | | | |
|---|---|---|---|
| 6,439,032 B1* | 8/2002 | Lehmann | 73/49.3 |
| 6,513,366 B1* | 2/2003 | Stauffer | 73/49.3 |
| 6,687,622 B2* | 2/2004 | Parker | 702/36 |
| 7,313,944 B2* | 1/2008 | Lehmann | 73/49.3 |
| 7,665,346 B1* | 2/2010 | Stauffer et al. | 73/49.3 |
| 8,544,315 B2* | 10/2013 | Guazzo et al. | 73/40.7 |
| 2005/0010175 A1* | 1/2005 | Beedon et al. | 604/218 |
| 2009/0241644 A1* | 10/2009 | Bonfiglioli | 73/49.3 |
| 2010/0274179 A1* | 10/2010 | Derichs | 604/33 |
| 2011/0174060 A1 | 7/2011 | Guazzo et al. | |
| 2014/0288408 A1* | 9/2014 | Deutsch | 600/407 |

* cited by examiner

METHOD AND APPARATUS FOR CHECKING SYRINGE BODIES

This application claims priority to Italian Patent Application BO2013A000128 filed Mar. 26, 2013, the entirety of which is incorporated by reference herein.

BACKGROUND OF THE INVENTION

This invention relates to a method and an apparatus for checking syringe bodies, where by "syringe body" is meant at least the main portion of a syringe containing the liquid product to be injected, that is to say, the cylindrical body of glass or plastic and the rear sliding seal (known as "plunger" in technical jargon) of rubber, defining a fluid seal with the inside surface of the cylindrical body. Further, the invention applies in particular to checking syringes of the ready-to-use, single dose type, containing a dose of liquid ready for injection.

The syringe bodies, usually without the needle and the plunger rod (the part acted upon by the user and coupled to the plunger or seal) are normally tested before going to market in order to check their fluid tightness to guarantee they are leakproof.

To do this, the syringe bodies are placed in an atmosphere under negative pressure allowing any leakage sites to be detected.

This operation exposes the entire outside surface of the syringe body to the pneumatic negative pressure and this may cause the rubber seal or plunger to withdraw towards the rear end of the cylindrical body. Under certain conditions, this withdrawal may cause the seal and/or the liquid to come into contact with parts of the syringe body which are not sterile, resulting in contamination and making the product permanently unfit for use.

SUMMARY OF THE INVENTION

In this context, the technical purpose of this invention is to propose a method and an apparatus for checking syringe bodies to overcome the above mentioned drawback.

More specifically, the aim of this invention is to provide a method and an apparatus for checking syringe bodies and able to prevent irreversible damage to the syringe bodies being checked, thus increasing the efficiency of the checking operation.

The technical purpose indicated and the aim specified are substantially achieved by a method for checking syringe bodies and by an apparatus for checking syringe bodies according to the description herein.

BRIEF DESCRIPTION OF THE DRAWINGS

The technical features of the invention, according to the above aim, are clearly described in the appended claims and its advantages are more apparent from the detailed description which follows, with reference to the accompanying drawings which illustrate a non-limiting example embodiment of the invention and in which:

DESCRIPTION OF THE PREFERRED EMBODIMENTS

Figure 1:
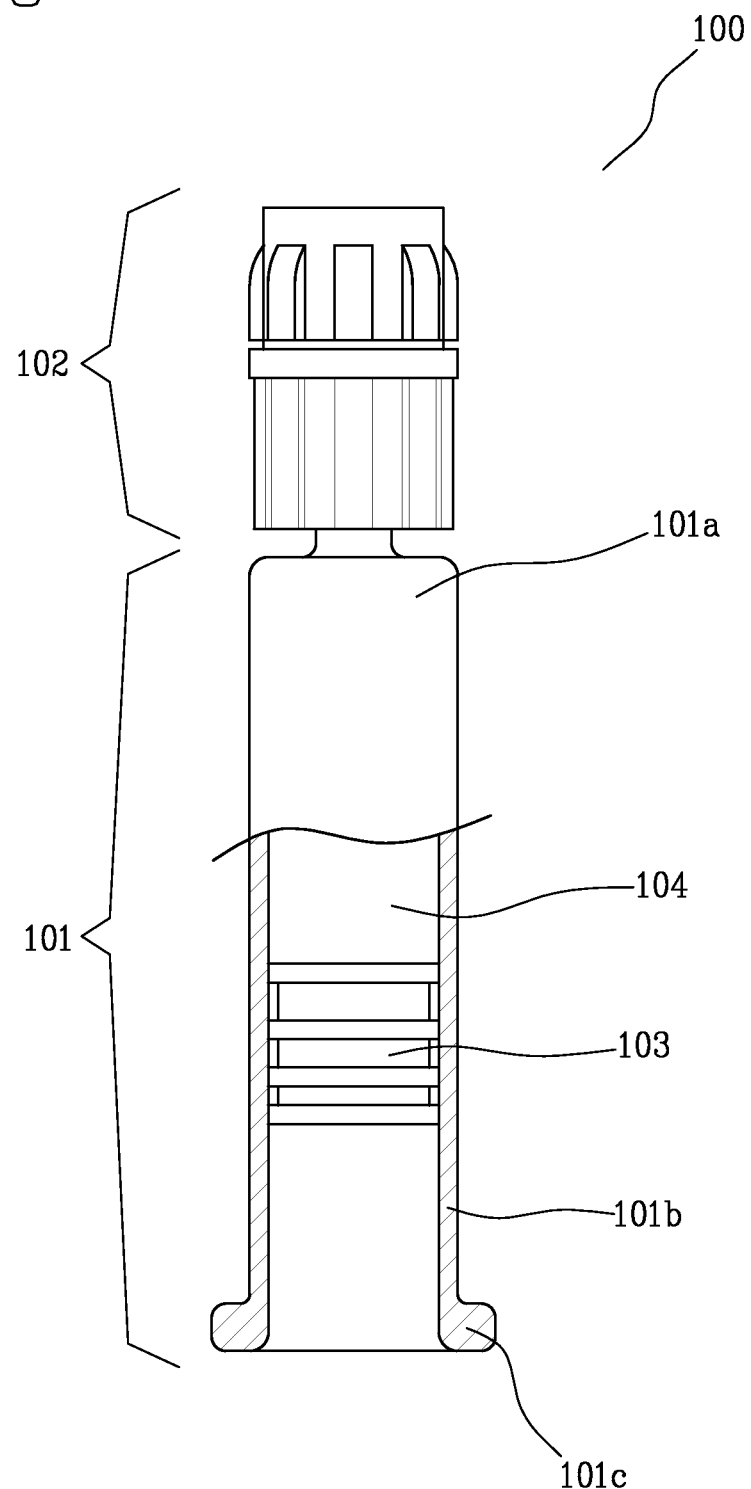
FIG. 1 shows a syringe body of the type which can be checked according to this invention.
Figure 2:
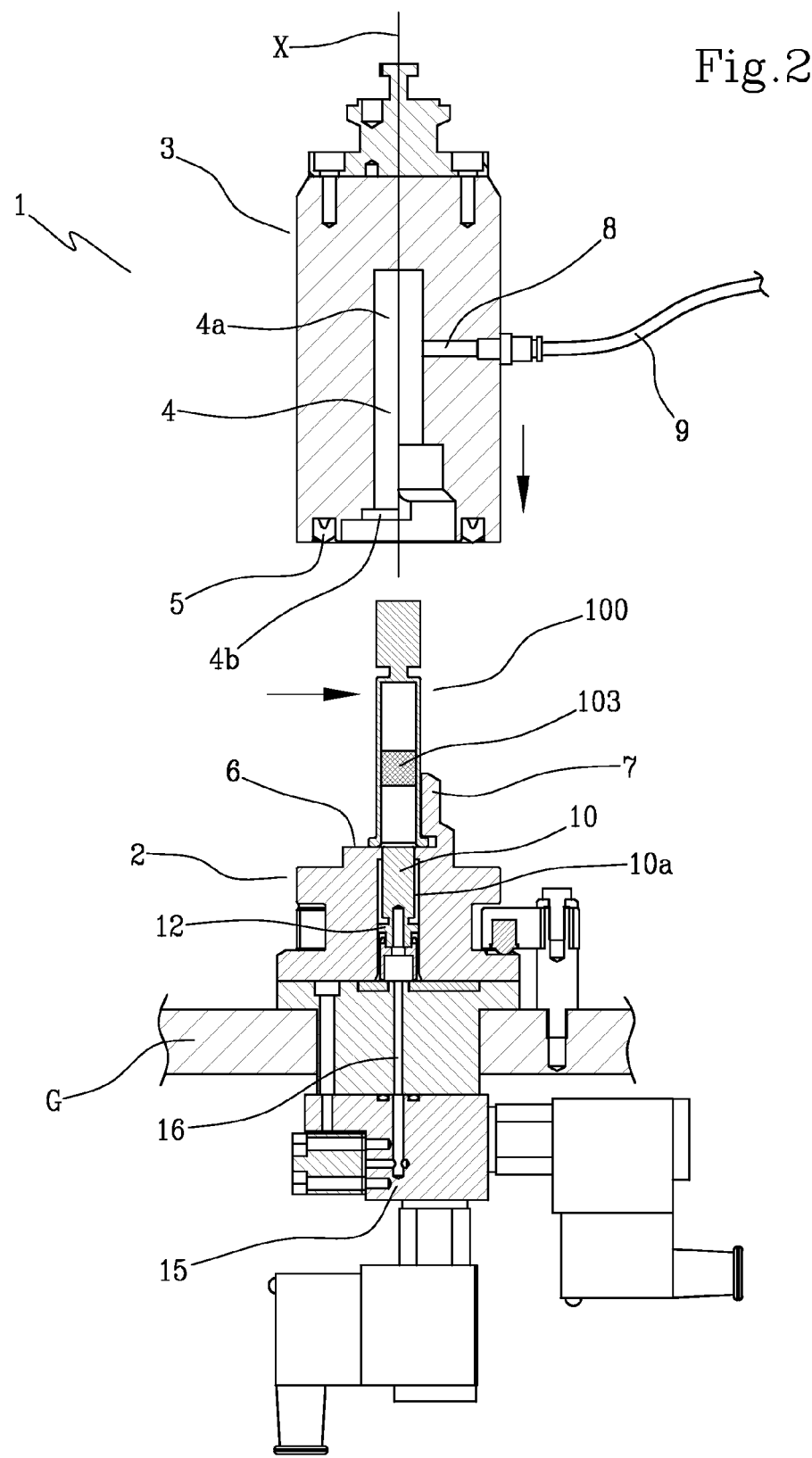
FIGS. 2-5 illustrate the apparatus according to the invention in a cross section through a vertical plane and in four successive operating steps of the method according to the invention.

With reference to FIG. 1, the numeral 100 denotes in its entirety a syringe body, preferably a single-dose syringe body, of the type which can be checked according to the invention.

The syringe body 100 comprises a hollow tubular body 101, preferably circular in cross section, having a front end 101a and a rear end 101b, the latter being preferably provided with a protruding rim 101c defining a projection relative to the outside surface of the hollow body 101. Applied to the front end 101a of the hollow body 101 there is an injection head 102 (of essentially known type) to which a needle, not illustrated, can be applied.

Slidably housed inside the hollow body 101 (also in known manner) there is a seal or plunger 103 which, in conjunction with the inside of the hollow body 101, defines a chamber 104 containing a predetermined dose of a liquid (for example a drug). The seal 103 can be moved by means of a plunger rod which can be pressed with a finger and which is not illustrated because for the purposes of implementing this invention, this plunger rod must be absent for reasons which will become clearer as this description continues.

The seal 103 hermetically seals the chamber 104 and the quality of that seal (as well as the seal of other parts of the syringe body 100, such as, for example, the injection head 102), is tested by an apparatus, which will now be described, and by which the syringe body 100 is checked according to the invention.

The apparatus 1 is preferably mounted on a rotary carousel (a part of which is labeled "G" in FIGS. 2-5) which is equipped, on its outer periphery, with a plurality of the apparatuses 1. Preferably, the carousel rotates about a vertical axis to move the checking apparatuses 1 cyclically between an infeed station, where the syringe bodies 100 are placed sequentially on respective checking apparatuses 1, and an outfeed station, where the syringe bodies 100, once checked, are removed from the carousel.

FIGS. 2-5 illustrate a checking device 1 according to the invention in successive operating steps.

More in detail, the device 1 comprises a base 2, integral with the frame of the carousel, and a hood 3 which can be stably coupled to the base 2 in such a way that when the hood 3 is coupled to the base 2, a hermetically sealed space 4 is formed between them. To improve the hermetic seal of the space, a peripheral seal 5 is interposed in the interface between the base 2 and the hood 3, preferably applied to a corresponding groove formed on the hood 3.

The base 2 and the hood 3 thus form part of a containment structure, denoted in its entirety by the reference character A, whose function is to internally define the hermetically sealed space 4. More specifically, separating the hood 3 from the base 2 allows access to the space 4, in particular to insert into the space a syringe body 100 so it can be checked, or to extract a syringe body 100 which has already been checked.

Other solutions for the containment structure A are imaginable, however, provided always that they allow access to the internal space 4.

The space 4 is preferably substantially shaped to match the outside shape of the syringe body 100 to be checked (with a minimum of clearance between the syringe body 100 and the hood 3 in order to facilitate spreading the pneumatic negative pressure throughout the space 4). More specifically, the space 4 has a cylindrical main portion 4a, shaped substantially to match the hollow body 101 and the injection head 102 of the syringe body 100, and a wide bottom 4b to receive the projecting rim 101c of the syringe body 100. The main portion 4a of the space thus has a main axis of extension "X" which is preferably vertical.

In the embodiment illustrated, the base 2 has a supporting surface 6 at the top of it on which the rim 101c of the syringe body 100 rests directly. The supporting surface 6 is preferably shaped to allow the syringe body 100 to be slidably loaded onto the base 2 along the supporting surface 6 itself. Preferably, also, the base 2 may have a supporting protrusion 7 to define a predetermined position for supporting the syringe body 100 on the base 2, suitable for subsequent application of the hood 3 to the base 2 in such a way that the hood 3 is correctly fitted over the syringe body 100.

In the configuration illustrated, therefore, the space 4 is almost entirely delimited by the hood 3, whilst the base contributes to delimiting the bottom of the space 4 and a part of the lateral surface of the same by means of the aforementioned supporting protrusion 7. Solutions other than that illustrated are possible, however.

The containment structure A also comprises an activation conduit 8 in fluid communication with the space 4 and connectable to a source of pneumatic negative pressure (for example, by way of a respective pipe 9) for activating a step of checking a syringe body 100 located inside the space 4.

In the embodiment illustrated in FIGS. 2-5 the activation conduit 8 is formed on the hood 3. It might also be formed on the base 2, however.

Fluid communication between the space 4 and the source of pneumatic negative pressure is turned on and off by means of an electronically controlled valve (not illustrated) driven by a control system.

The containment structure A comprises stop body 10 movable away from and towards the space 4 for achieving at least:
  a first operating position (FIG. 4) where it is at least partially facing inside the space 4 to define a stop which receives in abutment the seal 103 of the syringe body 100; and
  a second inactive position (FIG. 3) where it is further away from the space compared with the first position for allowing insertion and extraction of a syringe body 100 into/from the space 4.

The stop body 10 is movable between the first position and the second by translating along an axis parallel to, and preferably coinciding with, the axis of extension "X" of the main portion 4a of the space 4.

Figure 6:
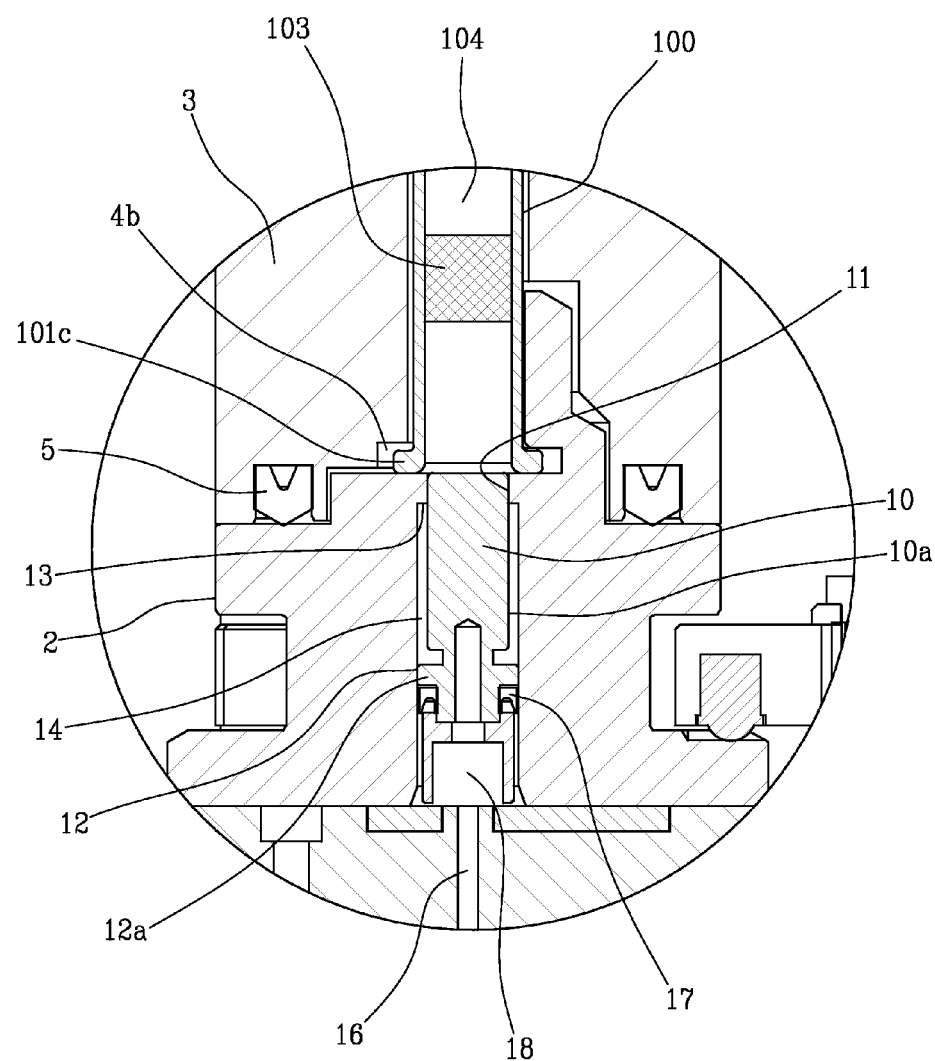
FIG. 6 shows an enlarged detail of the apparatus according to the invention in the operating position of FIG. 3.

More in detail, as also shown in FIG. 6, the stop body 10 has at least one cylindrical portion 10a which slides inside a corresponding hole 11 in the containment structure A and which is designed to come directly into abutment against the seal 103 of the syringe body 100.

Preferably, the diameter of the cylindrical portion 10a is just less than the inside diameter of the hollow body 101 of the syringe body 100. In effect, in order to be able to come into abutment against the seal 103, the cylindrical portion 10a must be able to be inserted into the rear part of the hollow body 101 (the seal 103 is generally located in the hollow body 101 at an intermediate position such as to leave a rear stretch of the hollow body 101 accessible from the outside).

In a preferred embodiment of the invention, the inside diameter of the hollow body 101 differs by about 2 mm from the outside diameter of the cylindrical portion 10a of the stop body 10. This allows the pneumatic negative pressure to be applied to the seal 103 as a whole, in particular at the interface between it and the inside wall of the hollow body 101, even in a configuration where the stop body 10 abuts against the seal 103 itself. In other words, the transversal cross section of the stop body 10 is such that at least a part of the seal 103 is always exposed to the pneumatic negative pressure.

The dimensions of the stop body 10, of the base 2 and of the hood 3 may change as a function of the size of the syringe to be tested, since diverse heights diameters are admissible. Depending on these differences, the stop device 10 is sized to generate a force equal and opposite to the force applied by the seal 103 when subjected to negative pressure, in order to hold it in place.

The stop body 10 also has a contact portion 12 designed to be engaged in abutment against a corresponding shoulder 13 defined by the containment structure A to form a limit stop of the stop body 10 on the contact portion 12 (FIG. 6) defined by a protrusion 12a, preferably annular, made on the stop body 10 and having a diameter which is larger than the outside diameter of the cylindrical portion 10a. Thus, the annular protrusion 12a can slide in the auxiliary chamber 14 together with the cylindrical portion 10a until reaching a limit position where it abuts the shoulder 13, a limit stop whose dimensioning relative to the working position and sole function are such as to prevent extraction in the event of an assembly error where there is no seal 103 inside the syringe body 100.

Advantageously, the stop body 10 may be left free to slide without the action of mechanical movement means (in other words, it may be "idle" or free at least relative to a movement towards the syringe body 100). In this situation, the stop body 10 may advantageously be moved towards the syringe body 100 by a withdrawing action applied by the selfsame negative pressure inside the space 4 by way of the activation conduit 8. More in detail, at the second position (inactive), the stop body 10 is preferably positioned with its front surface substantially aligned with the supporting surface 6 defined by the base.

Preferably, on the stop body 10 there may be an auxiliary seal 17 designed to create a fluid seal between the auxiliary chamber 14 (which has the same negative pressure as the space 4 to which it is connected) and a bottom chamber 18.

Preferably, withdrawing means 15 are also provided which act on the stop body 10 in order to move the stop body 10 from the first position to the second. Activation of the withdrawing means 15 and activation of the pneumatic negative pressure inside the space 4 are mutually exclusive, the former being opposed to the upward withdrawing action applied by the negative pressure in the space 4.

More specifically, the checking device 1 comprises a control system configured in such a way as to:
  activate the pneumatic negative pressure in the activation conduit 8 for starting a step of checking a syringe body 100 placed in the space 4; and
  activate the withdrawing means 15 simultaneously with or after deactivation of the pneumatic negative pressure in the activation conduit 8.

As mentioned above, the two activation steps just listed must occur at different times, preferably never simultaneously.

In the embodiment illustrated, the withdrawing means 15 comprise an auxiliary conduit 16 connectable to a source of pneumatic negative pressure and connected, through an auxiliary chamber 14 (and in particular through the second part, at the bottom in FIGS. 2-5, of the auxiliary chamber 14), to an end of the stop body 10 opposite the space 4.

In one embodiment a single source of pneumatic negative pressure is used both to create the negative pressure in the space 4 through the activation conduit 8 and to create the negative pressure in the auxiliary chamber 14 through the auxiliary conduit 16. This solution requires the provision of specific control valves driven by the aforementioned control system.

In a different embodiment, the movement of the stop body 10 might also be obtained by blowing compressed air into the chamber 18 through the conduit 16 (in addition to the aforementioned withdrawing action resulting from the negative pressure at the top). In use, a syringe body 100 is inserted into the space 4 which is hermetically sealed by applying and locking the hood 3 over the base 2.

Figure 3:
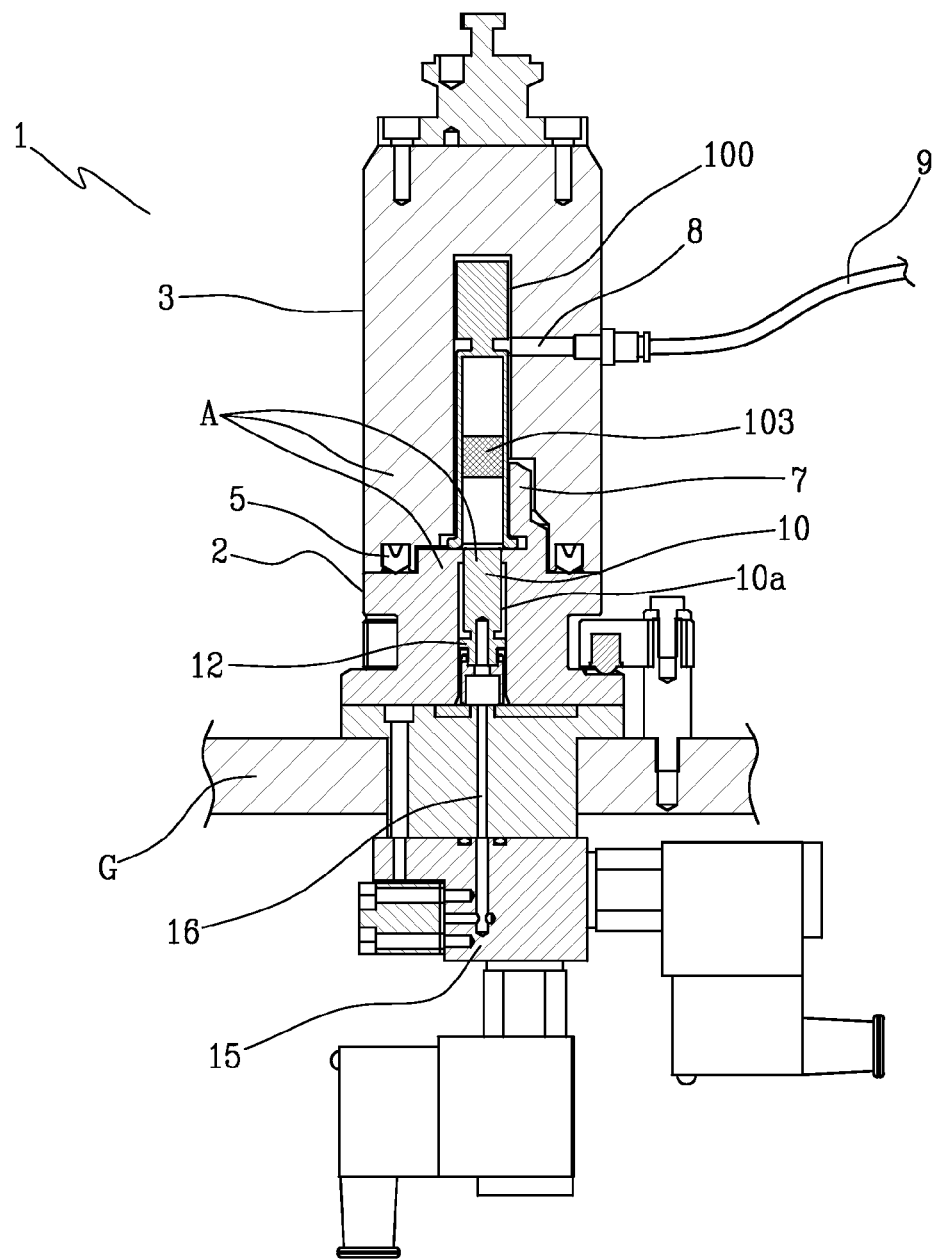

More specifically, first the syringe body 100 is placed on the supporting surface 6 of the base 2 (FIG. 2), for example by automated movement means located in the infeed station for the syringe bodies 100, and then the hood 3 is applied to the base 2 in such a way as to hermetically seal the space 4 relative to the outside (FIG. 3).

Next, a pneumatic negative pressure is applied to the syringe body 100 through the activation conduit 8 which carries the pneumatic negative pressure to the space 4, surrounding the outside of the syringe body 100, and also to the chamber 14 as far as the seal 17.

Figure 4:
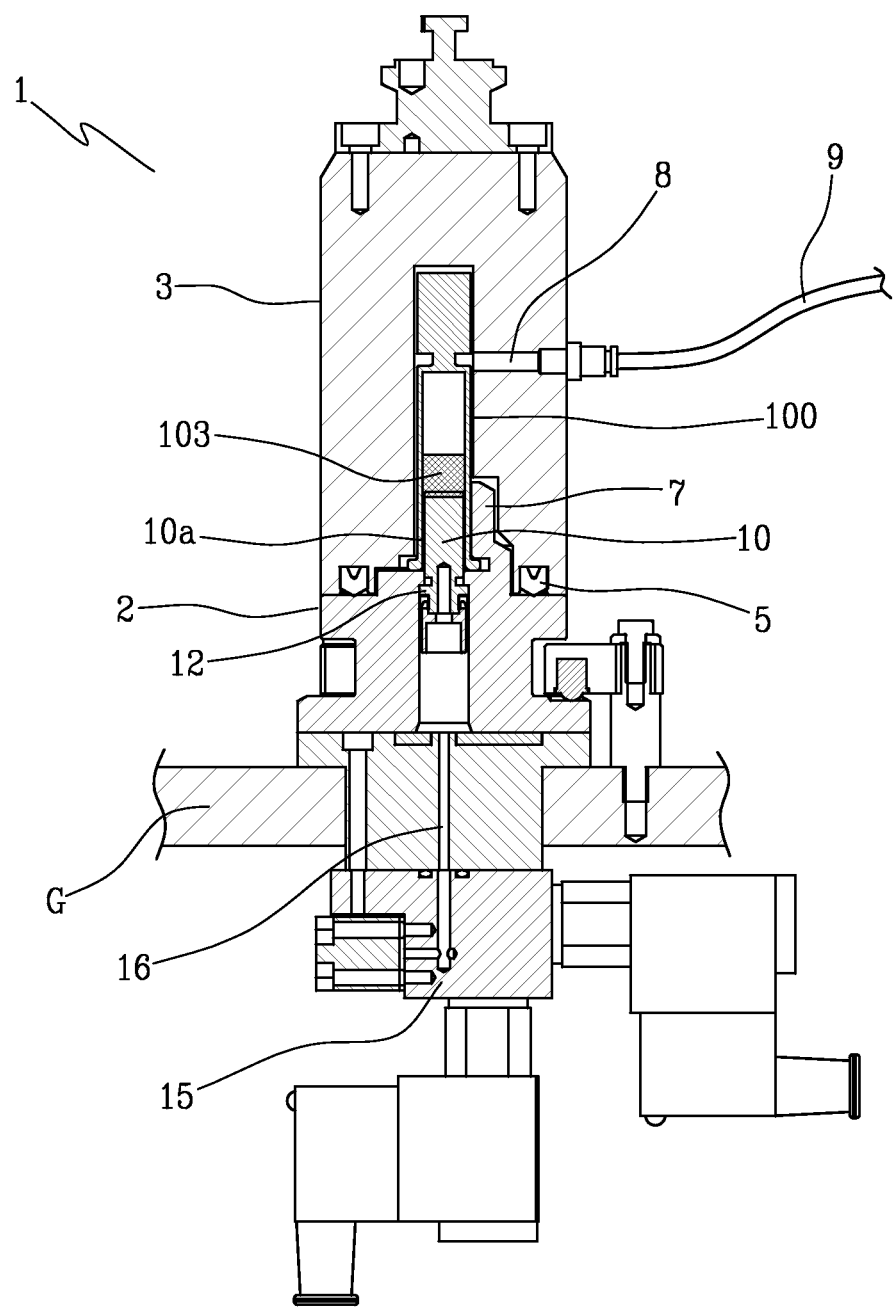

As a result of the pneumatic negative pressure generated, the stop body 10 is automatically withdrawn towards the syringe body 100 thanks to the resultant of the thrust forces applied by the pneumatic negative pressure on the selfsame stop body 10, (FIG. 4). This draws the stop body 10 towards the seal 103, preventing the seal 103 from being displaced to an excessive extent relative to the hollow body 101. Based on experiments, it has been found that a negative pressure of approximately −980 mbar (approximately 20 mbar absolute) allows the seal 103 a maximum displacement of less than 1 mm.

The automatic movement of the stop body 10 towards the syringe body 100 ends when the front part of the stop body 10 comes into abutment against the seal 103, preventing its sliding relative to the hollow body 101.

Preferably, the pneumatic negative pressure inside the space remains for a predetermined length of time (long enough to allow the syringe body 100 to be correctly checked) which is a function of the leak resistance to be detected, but preferably not less than 2.5 seconds. The aforementioned operation of the stop body 10 is able to stop the seal 103 from sliding for the full length of time following the reaching of the first (operating) position by the stop body 10 itself.

Figure 5:
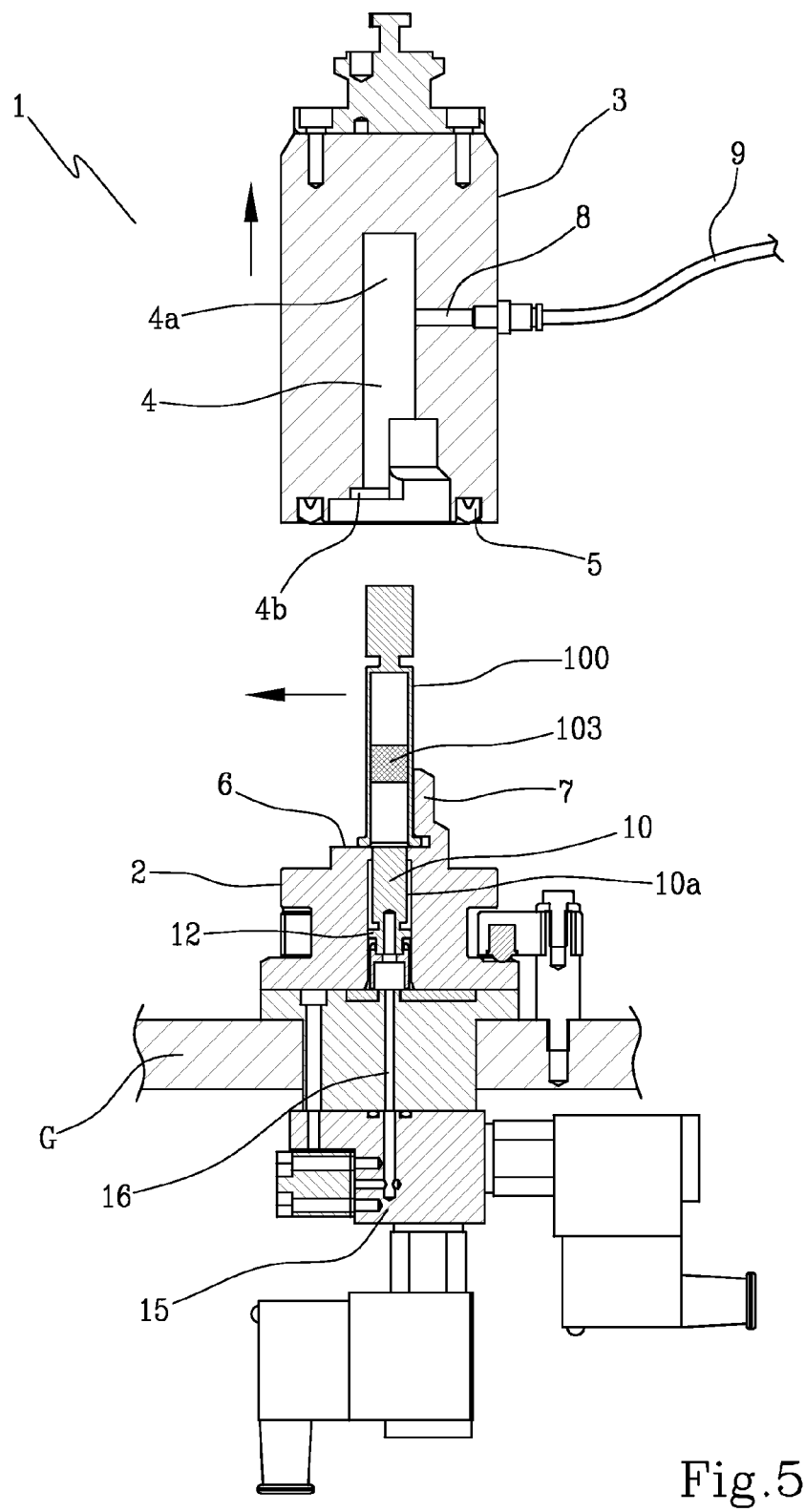

Simultaneously with or after deactivation of the pneumatic negative pressure inside the space 4, the withdrawing means 15 are activated which cause the stop body 10 to withdraw to the second (inactive) position, where the stop body 10 preferably disengages the space 4 in such a way as to allow the syringe body 100 to be removed from the space 4 (after opening the hood 3, as shown in FIG. 5).

In a different application of the system described above, this type of test device might also be used in laboratory equipment or machines, where the product to be tested can be positioned and covered with the hood manually.

This invention achieves the proposed aim by overcoming the above mentioned drawbacks of the prior art.

In effect, the checking device and method according to the invention allow holding the seal or plunger in place, or in any case keeping its displacement within acceptable limits, for the whole time the syringe body remains exposed to the negative pressure inside the test space. It follows that the seal or plunger is prevented from being displaced to any such extent as would negatively affect the sterility of the syringe body.

This eliminates the risk of irreversible damage to the syringe bodies during testing.

What is claimed is:

1. A method for checking a syringe body comprising a hollow body, a seal for closing the hollow body and a dose of a liquid product enclosed by the hollow body and by the seal, the method comprising:
   preparing a syringe body;
   applying a pneumatic negative pressure to the syringe body;
   preparing a stop body; and
   moving the syringe body and the stop body towards each other in such a way that, during at least a part of the step of applying the pneumatic negative pressure, the stop body obstructs withdrawal of the seal towards a rear end of the syringe body opposite the liquid product;
   wherein the moving the syringe body and the stop body towards each other is carried out by moving the stop body so that the stop body is positioned substantially in contact with the seal of the syringe body;
   wherein the movement of the stop body is obtained by making the stop body free at least relative to a movement towards the syringe body and exposing the stop body to the same pneumatic negative pressure applied to the syringe body such that the stop body is brought towards the syringe body by the pneumatic negative pressure.

2. The method according to claim 1, wherein the movement of the stop body is obtained by making the stop body free at least relative to a movement towards the syringe body and subjecting the stop body to thrust generated by pressure inside a chamber facing at least a bottom portion of the stop body.

3. The method according to claim 2, and further comprising moving the stop body away from the syringe body at an end of the applying the pneumatic negative pressure to the syringe body.

4. The method according to claim 1, and further comprising moving the stop body away from the syringe body at an end of the applying the pneumatic negative pressure to the syringe body.

5. An apparatus for checking a syringe body comprising a hollow body, a seal for closing the hollow body and a dose of a liquid product enclosed by the hollow body and by the seal, the apparatus comprising:
   a containment structure defining internally a hermetically sealed space configured to contain the syringe body to be checked;
   wherein the containment structure includes at least one activation conduit in fluid communication with the space and connectable to a source of pneumatic negative pressure for activating a step of checking the syringe body located inside the space;
   the containment structure comprising a stop body movable away from and towards the space for achieving at least:
   a first operating position where the stop body is at least partially facing inside the space to define a stop which receives in abutment the seal of the syringe body; and
   a second inactive position where the stop body is further away from the space compared with the first position for allowing insertion and extraction of the syringe body into/from the space;
   wherein the containment structure also includes a withdrawing mechanism acting on the stop body for moving the stop body from first position to the second position, and wherein the apparatus further comprises a control system configured in such a way as to selectively activate:

a pneumatic negative pressure it the activation conduit for starting the step of checking the syringe body placed in the space; or the withdrawing mechanism, simultaneously with or after deactivation of the pneumatic negative pressure in the activation conduit.

6. The apparatus according to claim 5, wherein the space has at least one cylindrical portion substantially shaped to match the hollow body of the syringe body, and wherein the stop body is movable between the first position and the second position by translating along an axis parallel to, and preferably coinciding with, an axis of extension of the at least one cylindrical portion of the space.

7. The apparatus according to claim 6, wherein the withdrawing mechanism comprises an auxiliary conduit connectable to the source of pneumatic negative pressure and connected, through an auxiliary chamber, to an end of the stop body opposite the space.

8. The apparatus according to claim 7, wherein the stop body has at least one cylindrical portion, translating inside a corresponding hole made in the containment structure, and a contact portion configured to form a limit stop of the stop body in the passage from the second position to the first position; the contact portion being engageable in abutment against a corresponding shoulder made on the containment structure.

9. The apparatus according to claim 8, wherein the containment structure comprises a base and a hood which can be stably coupled to the base for closing in a hermetically sealed fashion the space, wherein separation of the hood from the base allows access to the space for containment of the syringe body and wherein the hole in which the stop body slides is made on the base.

10. The apparatus according to claim 5, wherein the withdrawing mechanism comprises an auxiliary conduit connectable to the source of pneumatic negative pressure and connected, through an auxiliary chamber, to an end of the stop body opposite the space.

11. The apparatus according to claim 5, wherein the stop body has at least one cylindrical portion, translating inside a corresponding hole made in the containment structure, and a contact portion configured to form a limit stop of the stop body in the passage from the second position to the first position; the contact portion being engageable in abutment against a corresponding shoulder made on the containment structure.

12. The apparatus according to claim 11, wherein the containment structure comprises a base and a hood which can be stably coupled to the base for closing in a hermetically sealed fashion the space, wherein the separation of the hood from the base allows access to the space for containment of the syringe body and wherein the hole in which the stop body slides is made on the base.

13. An apparatus for checking a syringe body comprising a hollow body, a seal for closing the hollow body and a dose of a liquid product enclosed by the hollow body and by the seal, the apparatus comprising:

a containment structure defining internally a hermetically sealed space configured to contain the syringe body to be checked;

wherein the containment structure includes at least one activation conduit in fluid communication with the space and connectable to a source of pneumatic negative pressure for activating a step of checking the syringe body located inside the space;

the containment structure comprising a stop body movable away from and towards the space for achieving at least:

a first operating position where the stop body is at least partially facing inside the space to define a stop which receives in abutment the seal of the syringe body; and a second inactive position where the stop body is further away from the space compared with the first position for allowing insertion and extraction of the syringe body into/from the space;

wherein the stop body has at least one cylindrical portion, translating inside a corresponding hole made in the containment structure, and a contact portion configured to form a limit stop of the stop body in the passage from the second position to the first position; the contact portion being engageable in abutment against a corresponding shoulder made on the containment structure.

14. The apparatus according to claim 13, wherein the containment structure comprises a base and a hood which can be stably coupled to the base for closing in a hermetically sealed fashion the space, wherein separation of the hood from the base allows access to the space for containment of the syringe body and wherein the hole in which the stop body slides is made on the base.

15. A method for checking a syringe body comprising a hollow body, a seal for closing the hollow body and a dose of a liquid product enclosed by the hollow body and by the seal, the method comprising:

preparing a syringe body;

applying a pneumatic negative pressure to the syringe body;

preparing a stop body; and moving the syringe body and the stop body towards each other in such a way that, during at least a part of the step of applying the pneumatic negative pressure, the stop body obstructs withdrawal of the seal towards a rear end of the syringe body opposite the liquid product;

wherein the moving the syringe body and the stop body towards each other is carried out by moving the stop body so that the stop body is positioned substantially in contact with the seal of the syringe body;

wherein the movement of the stop body is obtained by making the stop body free at least relative to a movement towards the syringe body and subjecting the stop body to thrust generated by pressure inside a chamber facing at least a bottom portion of the stop body.

\* \* \* \* \*